(12) United States Patent
Diokno et al.

(10) Patent No.: US 6,569,091 B2
(45) Date of Patent: May 27, 2003

(54) DISCONNECTABLE VAGINAL SPECULUM WITH REMOVEABLE BLADES

(76) Inventors: Ananias Diokno, 480 Hillspur Rd., Ann Arbor, MI (US) 48105; German Borodulin, 583 46th Ave., San Francisco, CA (US) 94121; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 0 days.

(21) Appl. No.: 09/977,029

(22) Filed: Oct. 15, 2001

(65) Prior Publication Data

US 2002/0022771 A1 Feb. 21, 2002

Related U.S. Application Data

(63) Continuation of application No. 09/565,613, filed on May 4, 2000.

(51) Int. Cl.[7] .................................................. A61B 1/32
(52) U.S. Cl. ...................... 600/220; 600/205; 600/222; 600/223; 600/224
(58) Field of Search ................................ 600/202, 205, 600/220, 221, 222, 215, 223, 224, 219, 235, 245

(56) References Cited

U.S. PATENT DOCUMENTS

| 6,024,697 | A | * | 2/2000 | Pisarik .......................... 600/224 |
| 6,364,832 | B1 | * | 4/2002 | Propp ........................... 600/220 |
| 6,379,299 | B1 | * | 4/2002 | Borodulin et al. ........... 600/220 |
| 6,450,952 | B1 | * | 9/2002 | Rioux et al. ................. 600/223 |

* cited by examiner

*Primary Examiner*—Pedro Philogene

(57) ABSTRACT

A vaginal speculum consists of two pivotally interconnected disconnectable parts. Each part slidingly supports a movable blade moveable in the longitudinal direction of the speculum. In addition to longitudinal movement, one of the blades can be moved circumferentially. Each blade can be completely withdrawn from the speculum, even during the procedure, i.e., without removing the speculum from the vagina. As a result, the same speculum can be used in procedures requiring both as well as only one blade. Furthermore, the entire upper part of the speculum, i.e., the guide portion together with the removable blade, can be completely disconnected from the speculum without removing the latter from the vagina. The remaining lower part can be used as a spatula. Circumferential displacement of one of the blades in both directions makes it possible to observe the vaginal cavity over the entire periphery without rotating the entire speculum or replacing it with another tool.

19 Claims, 3 Drawing Sheets

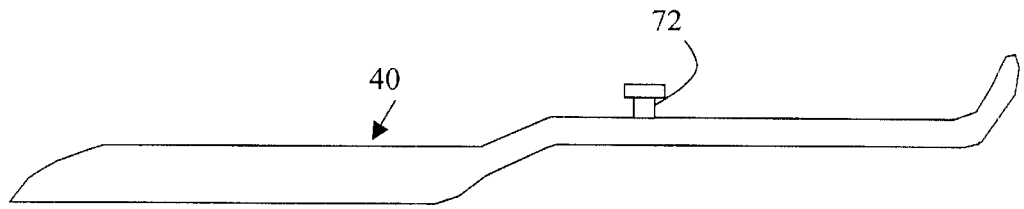
Fig. 5
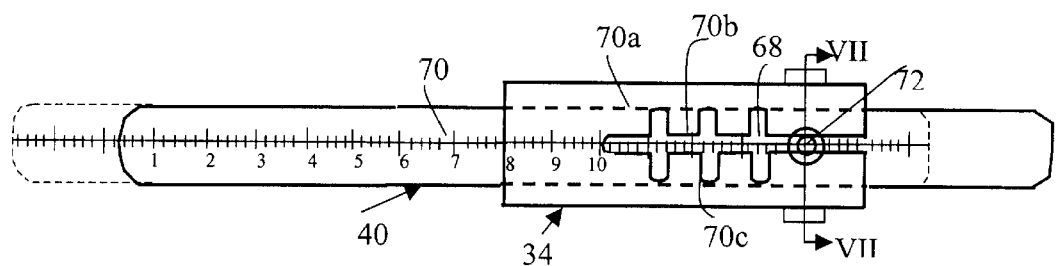
Fig. 6
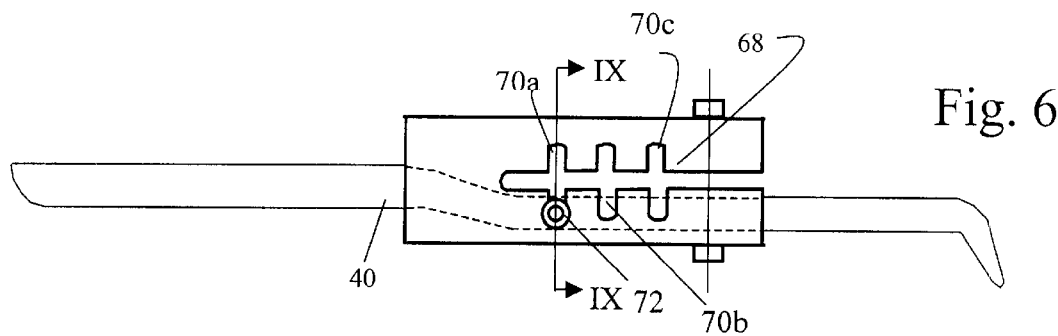
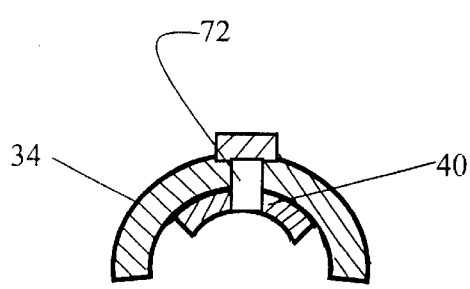
Fig. 7
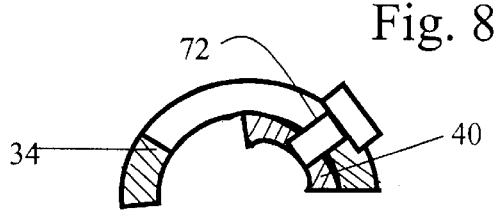
Fig. 8
Fig. 9

DISCONNECTABLE VAGINAL SPECULUM WITH REMOVEABLE BLADES

CROSS-REFERENCES TO RELATED APPLICATIONS

The present patent application is continuation of our previous U.S. patent application Ser. No. 09/565,613 filed on May 4, 2000, which is now pending.

FIELD OF THE INVENTION

The present invention relates to medical diagnostic instruments, in particular to a vaginal speculum for visual examination of the vaginal cavity, vaginal walls, and conditions of the cervix.

BACKGROUND OF THE INVENTION

A vaginal speculum is a diagnostic instrument for dilating the opening of the vagina cavity in order that the interior may be more easily visible for observation. A vaginal speculum has two expandable blades, which are inserted into the vagina in a closed state and then expanded, or moved apart for dilating the vaginal cavity. In particular, a vaginal speculum is an indispensable instrument not only for gynecologists but also for primary care physicians, geriatricians, urologists, and nurse practitioners for urological examination of patients suffering from urinary incontinence in order to exclude the presence of vaginal prolapses, such as rectocele, cystocele, enterocele, and uterine prolapse. Vaginal prolapses of the aforementioned type are protrusions or herniation of the urethra or other pelvic organs into the vagina.

DESCRIPTION OF THE PRIOR ART

One typical vaginal speculum is described in U.S. Pat. No. 3,716,047 issued in 1973 to W. C. Moore et al. The instrument consists of three parts of molded non-toxic plastic materials, i.e., a fixed member, a movable member, and a sliding member. The sliding member is slidingly installed in the fixed member and pivotally supports the movable member so that the movable member can be rotated around the pivot at the proximal end of the fixed member. As a result, the distal ends of the movable and fixed members, which form expandable blades insertable into the vagina, can dilate the vagina cavity and thus allow internal vaginal observations. The members are made from a transparent plastic and the blades form a thin-wall circular or oval cross-section, which allows the observation. In the context of the present invention, the term "distal" is used with regard to the end of the speculum remote from the user's hand, while the end on the side of the part 26 is referred to as a proximal end of the speculum.

A procedure of examination of a vagina with the use of a speculum involves movements of the speculum in an expanded, i.e., an outwardly diverging state in the direction towards or away from the uterus. This is necessary for diagnosing aforementioned vaginal prolapses. However, since the opening of the vagina has a circular muscle, which is more resistant to dilations than the vaginal cavity, the aforementioned withdrawal of the expanded speculum may cause in patient discomfort and painful sensations. This is because in the course of the withdrawal of the speculum the diameter of its portion at the vaginal opening is stretched by the speculum. Furthermore, the conventional vaginal specula do not have features for measuring the length of vagina and for testing and measuring the severity of the prolapses without completely removing the entire speculum. Normally, the physician disassembles the speculum and inserts only one of the blades for pressing on one wall of the vagina for exposing and observing the opposite wall. In case of prolapses, a separate ruler is used for measuring the length and position of the prolapse or prolapses. The procedure is then repeated for expositing the opposite wall of the vagina cavity. In some cases, the physician uses a separate single metal blade for pressing on the anterior and posterior walls of the vagina cavity. Thus, the examination involves the use of several tools, as well as assembling and disassembling operations. Thus, it is impossible with conventional specula to conduct more concentrated and localized examination of one wall of the vaginal cavity without removing them from the vagina and reinserting other tools one at a time. Such multiple maneuvers are not only very inconvenient and time-consuming but also irritating and uncomfortable to the patient.

Furthermore, the speculum of U.S. Pat. No. 3,716,047 does not allow for observation of the entire periphery of the vaginal cavity without rotating the speculum as a whole, which is undesired and inconvenient.

An attempt to solve a problem associated with possibility of observing the entire periphery of the vaginal cavity is described in U.S. Pat. No. 6,048,308 issued in 2000 to John Strong. The speculum described in this patent is provided with two additional blades insertable into the speculum housing for spreading apart in lateral direction required for observation of the side walls of the vaginal cavity. A disadvantage of this device is that it requires the use of two additional blades. These blades cannot be disconnected from the speculum without removing the latter from the vaginal cavity.

An attempt to solve the problems regarding adjustability of the blades in a longitudinal direction is partially solved in a vaginal speculum described in U.S. Pat. No. 2,579,849 issued in 1951 to Louis Newman. The speculum described in the above patent has blades adjustable in the longitudinal direction by extending their distal ends. The adjustable blades are guided in pivotally interconnected parts and cannot be completely removed from the speculum but can only be shifted forward to increase the blades' length. Since during the procedure the step formed at the point of protrusion of the adjustable portion from the guiding portion is located inside the vagina, there is a danger of pinching a mucosa during withdrawal of the adjustable blade towards the guide portion. The speculum of U.S. Pat. No. 2,579,849 does not allow for observing side walls of the vaginal cavity without completely removing it from the vagina and replacing with another instrument.

Furthermore, in examining the conditions of the cervix with the use of the aforementioned vaginal specula, it is difficult to diagnose cervical papilomas at the initial stage of their development. This is because such initial papilomas are very small. A papiloma is a growth pattern of epithelial tumors.

U.S. Pat. No. 2,579,849 issued to L. B. Newman in 1951 describes a vaginal speculum with adjustable blades which during the procedure are completely insertable into the vagina and only small distal tips thereof are adjusted inside the vagina. In other words, the adjustable blades of Newman are first inserted into the vagina and then could be adjusted in length by moving forward the distal ends of the blades. The Newman device is first inserted into the vagina only with its constant length and then can be slightly extended forward within the vagina. It can be seen from FIG. 3 of Newman's patent that the guide portions for the adjustable tips of Newman are completely inserted into the vagina and thus constitute the blades themselves.

The applicants made an attempt to solve the problems of the prior art by developing a vaginal speculum described in U.S. patent application Ser. No. 09/565,613 filed on May 4, 2000, now pending. The vaginal speculum described in the aforementioned patent application consists of two parts pivotally interconnected through a fork-like member. Each part slidingly supports a blade moveable in the longitudinal direction of the speculum so that each blade can be shifted to a required position and fixed in this position for further use. The removeable blades can be withdrawn partially or completely for replacement with blades of other dimensions without withdrawing the entire speculum from the vagina. In a closed state, the distal ends of the blades form a bifocal lens, which can be used for visually detecting changes, associated with an earlier stage of cancer or erosion. Provision of retractable blades makes it possible for a physician to withdraw the blades in an alternating sequence for exposing one of the walls of the vagina cavity by pressing down with the longer blade on the opposite wall. The blades are provided with a scale for measuring the positions and dimensions of the prolapses.

In spite of all the advantages, the vaginal speculum of U.S. patent application Ser. No. 09/565,613 still has some drawback. Though the removeable blades can be shifted to any required position and even completely removed or replaced, the pivotally connected parts that guide the blades are not disconnectable. In some cases, however, a procedure may require that the physician must use only one blade. To accomplish this task with any known vaginal speculum, including the one described in the last-mentioned patent application, the physician has to withdraw the entire speculum from the vagina and replace it with a single-blade instrument. Another disadvantage of the non-disconnectable speculum is that it is inconvenient for cleaning, storage, and packing. Furthermore, the blades can be moved only linearly in a longitudinal direction of the speculum and cannot be moved circumferentially for observation of side walls of the vaginal cavity without replacing, removing or rotating the entire speculum.

OBJECTS OF THE INVENTION

It is an object of the present invention to provide a vaginal speculum, in which one of the blade guide parts can be disconnected or the blade can be removed from the speculum without interrupting the procedure. Another object is to provide a vaginal speculum which is convenient for cleaning, storage and packing and which allows observation of the vaginal walls over the entire perimeter of the vaginal cavity without withdrawing, replacing or rotating the entire speculum. Another object is to provide a vaginal speculum having blades moveable in axial as well as in circumferential direction.

BRIEF DESCRIPTION OF THE DRAWINGS

FIG. 5 is a side view of a blade of FIG. 4.

FIG. 6 is a view similar to the one of FIG. 3 with the upper blade inserted.

FIG. 7 is a sectional view along line VII—VII of FIG. 6.

FIG. 8 is a view similar to the one of FIG. 6 with the upper blade turned circumferentially from the position shown in FIG. 6.

FIG. 9 is a sectional view along line IX—IX of FIG. 8.

SUMMARY OF THE INVENTION

Figure 1B:
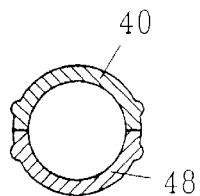
FIG. 1B is a sectional view along line IB—IB of FIG. 1A.

A vaginal speculum consisting of two pivotally interconnected disconnectable parts. Each part slidingly supports a blade moveable in the longitudinal direction of the speculum. In addition to longitudinal movement, one of the blades can be moved circumferentially. Each blade can be completely withdrawn from the speculum, even during the procedure, i.e., without removing the speculum from the vagina. As a result, the same speculum can be used in procedures requiring both as well as only one blade. Circumferential displacement of one of the blades in both directions makes it possible to observe the vaginal cavity over the entire periphery without rotating the entire speculum or replacing it with another tool.

DETAILED DESCRIPTION OF THE INVENTION

In general, a vaginal speculum of the present invention is similar to the one described in our U.S. patent application No. 09/565,613 and is aimed at its improvement. Therefore some small details of the vaginal speculum of the present invention identical to those in the speculum of the previous patent application will be omitted from the description.

As can be seen from FIG. 1A, which is a side elevation view of the speculum 20 of the invention, the speculum 20 consists of three main parts: a first part 22 (hereinafter referred to as an upper part), a second part 24 (hereinafter referred to as a lower part), and a third part 26, hereinafter referred to as a sliding part, which can slide in guides 28 formed on the rear side of the lower part 24 in a transverse direction shown by the arrow A with respect to the longitudinal direction of the vaginal speculum shown by the arrow B. The sliding part 26 has pins 30 and 32 (only one of which, i.e., a pin 30, is shown in FIG. 1A), which pivotally supports the upper part 22.

The upper part 22 has an L-shaped configuration with legs 34 and 36. The leg 34 extends in the direction of aforementioned arrow B, and the leg 36 extends downward substantially perpendicular to the leg 34. The leg 36 extends substantially in a downward transverse direction from the rear side of the leg 34 and is used for pushing on the upper part 22 when it is necessary to expand the speculum 20 inside the patient's vagina. The horizontal leg 34 of the upper part 22 has longitudinal guides 38 for an upper removable blade 40.

The lower part 24 also has an L-shaped configuration with a horizontal leg 42 and a downward vertical leg or handle portion 44. The leg 42 extends in the direction of aforementioned arrow B. The leg 42 has longitudinal guides 46 for a lower removable blade 48 that can move in the aforementioned guides 46 in the direction of arrow B. The aforementioned guides 28 for the sliding part 26 are located on the rear end face of the handle 44.

The sliding part 26 has a rearward projection 52, which is substantially perpendicular to the fork-like straight portion 54 and has teeth 56 on one of its sides. The teeth 56 engage a pawl 57 formed on the surface of the slot (not shown) formed in the leg 36. The sliding part 26 also has a tail portion 58 with a pawl 60 for engagement with ratchet teeth 62 formed in the lower rear side of the straight portion 54.

Figure 1A:
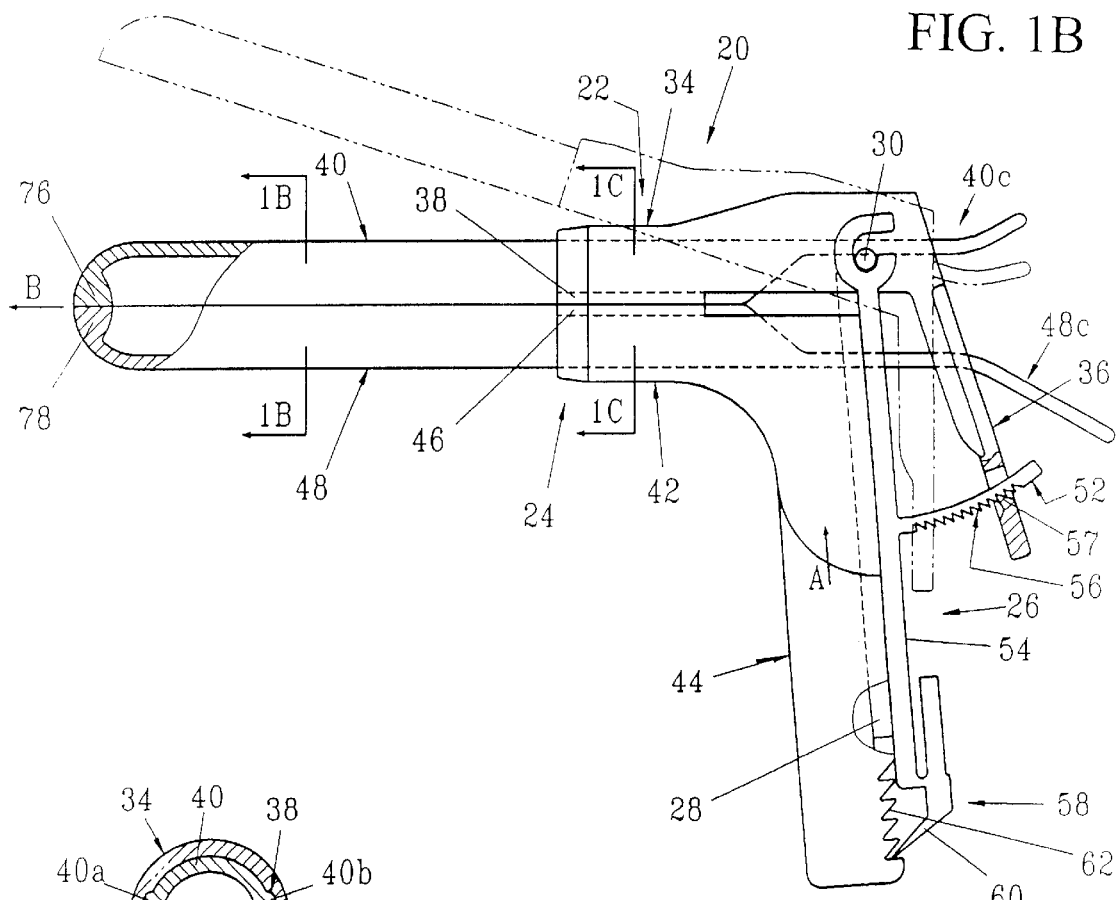
FIG. 1A is a side sectional elevation view of the vaginal speculum of the invention.

As can be seen from FIG. 1B, which is a cross-sectional view along line IB—IB of FIG. 1A, the removable blades 40 and 48 have semicircular cross sections so that in a closed state of the speculum shown FIG. 1, both removable blades form a hollow tubular body having a complete round cross-section.

Figure 1C:
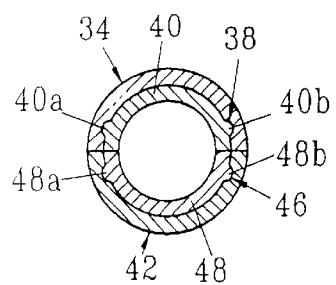
FIG. 1C is a sectional view along line IC—IC of FIG. 1A.

Furthermore, as can be seen from FIG. 1C, which is a cross-sectional view along line IC—IC of FIG. 1A, the aforementioned horizontal leg portions 34 and 42 also have semicircular cross-sections. It is shown in the same FIG. 1C that the aforementioned guides 38 and 46 are formed by radial outward grooves in the inner surface at the edges of the guide 38 and by radial outward grooves in the inner surface at the mating edges of the guide 42. On the other hand, the removable blades 40 and 48 have radial outward projections on the mating edges, i.e., projections 40a, 40b on the blade 40 and projections 48a, 48b on the blade 48. The projections 40a, 40b, 48a, 48b are rounded so that the outer surfaces of the blades remain smooth.

In order to provide rotation of the upper removable blade 40 by guiding in circumferential grooves described below, the guides 38 are formed on a part of length of the upper part 34, so that for rotation the blade 40 should be first moved forward away from the proximal part until the projections 40a and 40b are freed from the guides 38 and then the blade 40 can be easily rotated.

The proximal ends 40c and 48c of respective removable blades 40 and 48 are bent outward in the upper and lower directions, respectively, to form parts convenient for pushing on the respective blades 40 and 48 to move them forward or for pulling them away when it is required to withdraw or replace the respective blade.

Figure 2:
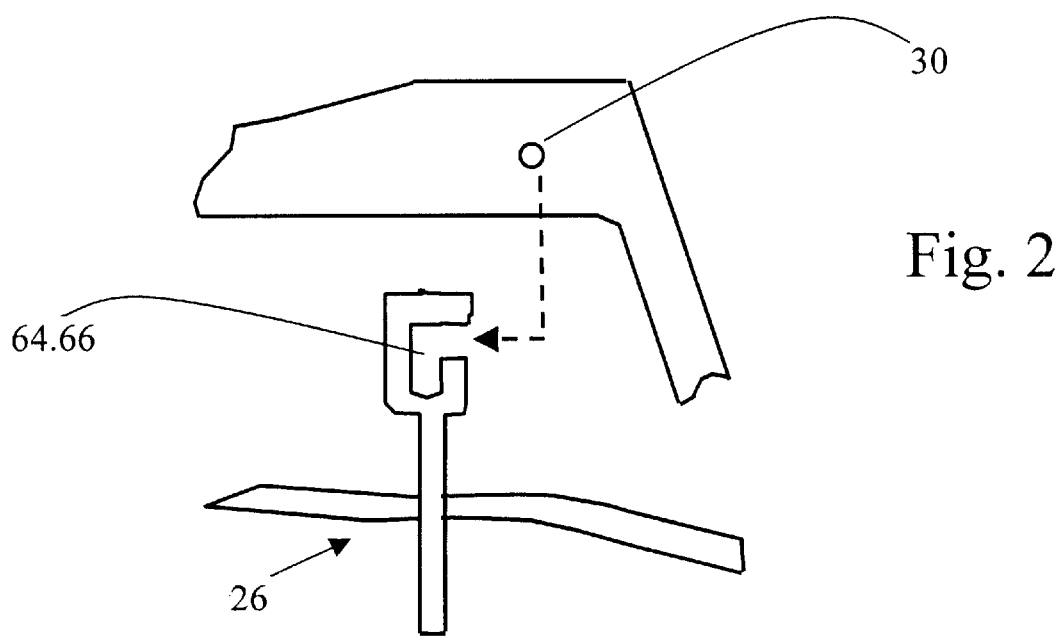
FIG. 2 is a partial side view of the speculum of FIG. 1A illustrating disassembling of main parts.
Figure 3:
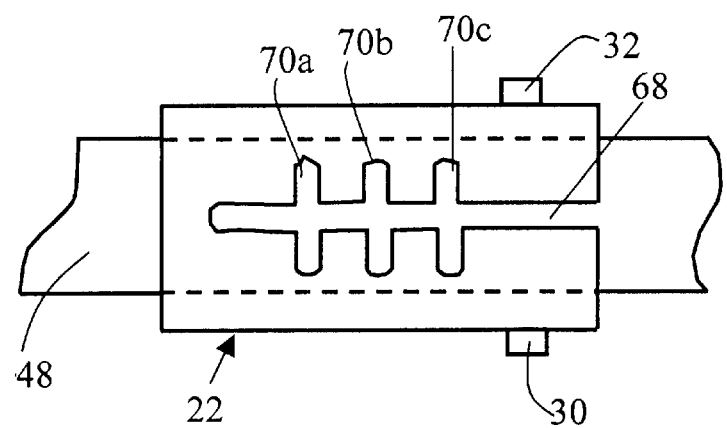
FIG. 3 is a top view on a part of the vaginal speculum of FIG. 1A with the upper blade removed.

A distinguishing feature of the vaginal speculum 20 of the present invention consists in that the entire speculum 20 can be disassembled, i. e., all three main parts, i.e., the upper part 22, the lower part 24, the sliding part 26, as well as the upper removable blade 40 and the lower removable blade 48 are disconnectable. More specifically, as shown in FIG. 1A and FIG. 2, which is a partial side view of the speculum of FIG. 1A with the lower part 24 disconnected from the upper part 22, the upper end of the fork-like sliding part 26 has hook-like shape with bayonet slots 64, 66 (the slot 66 is formed on the side of the fork-like part which is not seen in FIG. 2). The slots 64 and 66 serve for insertion of the pins 30 and 32. The pin 32 is seen in FIG. 3 which is a top view on a part of the vaginal speculum 20 of FIG. 1A with the upper removable blade 40 and the sliding part 26 removed. Arrows C in FIG. 2 show directions of assembling disassembling of parts 22 and 24.

Figure 4:
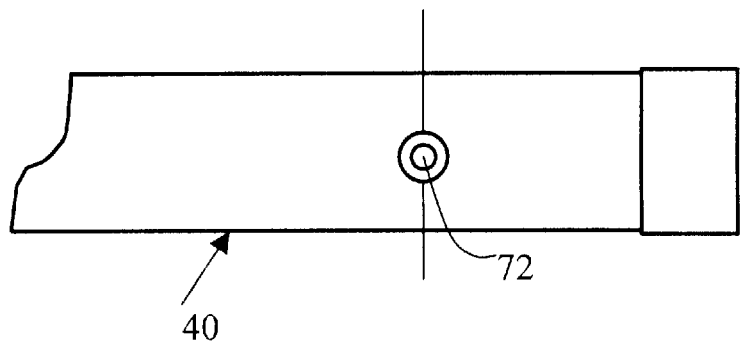
FIG. 4 is a top view on one of the removeable blades of the speculum of FIG. 1A.

Another unique feature of the vaginal speculum of the present invention consists in that in addition to movements in the axial direction shown by arrow B, at least one of the blades, e.g., the upper removable blade 40, can be turned circumferentially around the longitudinal axis coinciding with the of arrow B (FIG. 1A) of the speculum 20. This is achieved by forming a longitudinal slot and at least one circumferential slot in the upper surface in the rear side of the upper part 22 of the speculum (FIG. 3). Three such circumferential slots 70a, 70b, and 70c, which intersect the longitudinal slot 68, are formed in the embodiment shown in FIG. 3. The upper removable blade 40 has a vertical guide pin 72 shown in FIG. 4 which is a top view on one of the removable blades of the speculum of FIG. 1A. FIG. 5 is a side view of a blade of FIG. 4. FIG. 6 is a view similar to the one of FIG. 3 with the upper blade inserted. The pin 72 can be guided in the longitudinal slot 68 and in the circumferential slots 70a, 70b, and 70c, so that guiding in the longitudinal slot 68 defines axial movements of the upper blade 40 while guiding of the pin 72 in the circumferential slots 70a, 70b, and 70c defines rotation of the upper blade 40 around the longitudinal axis. Position of the pin 72 in the longitudinal slot 68 is shown in FIG. 7, which is a sectional view along line VII—VII of FIG. 6. FIG. 8 is a view similar to the one of FIG. 6 with the upper blade turned circumferentially from the position shown in FIG. 6 by guiding the pin 72 in the circumferential slot 70a, and FIG. 9 is a sectional view along line IX—IX of FIG. 8. Only upper guide part 22 and the upper removable blade 40 are shown in FIGS. 7 and 9.

Similar to the vaginal speculum of U.S. patent application Ser. No. 09/565,613, the speculum 20 of the present invention can be provided with a scale 74 formed on the upper removable blade 40 (FIG. 6). Similarly, the scale (not shown) can be formed on the lower blade 48. The scales can be used for measuring the positions and dimensions of the vaginal prolapses.

As shown in FIG. 1A, similar to the vaginal speculum of U.S. patent application Ser. No. 09/565,613, in the speculum of the present invention the distal end of the upper removable blade 40 has a half-lens 76, which is formed, e.g., molded, integrally with the remaining part of the blade 40. The half-lens 76, in fact, is a portion of a biconvex lens obtained by cutting a lens by half along an optical axis, which in this case coincides with longitudinal axis of the speculum. A similar half-lens 78 is formed at the distal end of the lower removable blade 48. As a result, in a closed state of the speculum 20, the blades 40 and 48 form a tubular body of a complete round or oval cross-section with a complete biconvex lens formed by two half-lenses 76 and 78 at the distal end of the speculum.

The vaginal speculum of the present invention is used in a manner described below.

Procedure for the Use of the Retractable Vaginal Speculum

The procedure is started from inspection of the vaginal introitus to determine the status of the vaginal skin, the size of the vaginal outlet, and the presence or absence of pelvic organ prolapse. A vaginal speculum 20 of the invention having a required size is then chosen.

Since this vaginal speculum 20 is normally a disposable instrument, which is sterilized and packed into a sealed package in the form of the upper part 22, a lower part 24, a sliding part 26, and removable blades 40 and 48, it is unpacked and removed from the package and is assembled from the aforementioned disconnectable part. More specifically, the sliding part 26 is inserted into the guides 28 formed on he rear side of the handle portion 44 of the lower part 24 of the speculum and is fixed on it be engaging the pawl 60 with the ratchet teeth 62. The upper part 22 is then pivotally connected to the sliding portion 26 by inserting pins 30 and 32 (FIGS. 2 and 3) into the slots 64, 66. The removable blades 40 and 48 are inserted into their respective guides 38 and 46 (FIGS. 1A and 1C) and fixed in a required position with the use of dimples on the inner surface of the upper part and of a projection (not shown) on the outer surface in the proximal part of the removable blade 40.

The speculum 20 is closed so that the blades 40 and 48 assume positions shown in FIG. 1C by solid lines. This is achieved by pushing the leg 36 in a counterclockwise direction around the pins 30 and 36 as fulcrum points. The removable blades are then lubricated using a water-soluble lubricant and gently inserted into the vaginal canal in the aforementioned closed state of the speculum. The blades 40 and 48 are advanced all the way to the vaginal vault or at the level of the uterine cervix (not shown).

The physician first visually observes the condition of the uterus cervix through the optical lens formed by semilenses 76 and 78.

The purpose of this observation is to detect initial changes on the cervix that could not be detected by a naked eye. Such changes may be initial erosion, papilomas, etc.

The speculum 20 is then opened by moving the blades 40 and 48 apart to further visualize the vaginal vault or the cervix. This is done by pushing on the trigger portion 36 to turn it in a clockwise direction around pins 30 and 32 so that the pawl 57 slides in a ratchet manner over the teeth 56 of the leg 36. As a result, the blade members 40 and 48 of the speculum 20 assume the positions shown in FIG. 1A by broken lines and thus expand the vaginal cavity (not shown in the drawings).

The physician can then observe the appearance of the vaginal mucosa at the level of the vault, or observe the appearance of the cervix. If necessary, the length of the vaginal canal is measured from the vaginal vault or the posterior aspect of the cervico-vaginal junction to the level of the hymenal line. This is achieved by pushing down on the tab 40c of the removable blade 40 for disengaging the dent from the respective indent (not shown) and by moving the blade 40 to a required position. Measurement is made by reading the numbers of the scale 74 with regard to the hymeneal line, as is described in our previous U.S. patent application Ser. No. 09/565,613. The speculum of the present invention can be provided with the same measurement system as the speculum of our aforementioned patent application and allows all the measurements described in detail in that application. As the measurement system and method are beyond the scope of the present patent application, their description is omitted.

If necessary, the physician performs paps smear and/or collection of fluids for culture and or cytology as indicated. Slight thickening of the curved end walls on the distal ends of the blades 20 and 22 caused by the formation of semilenses does not create any obstacles for this operation.

For separate observation of the condition of one of the walls of the vagina, the removable blade, e.g. blade 40 (FIGS. 1 and 5) is then retracted halfway so that only the blade 48 of the speculum 20 remains in the initial position. Since another blade 40 is partially withdrawn (these positions are not shown in the drawings), the physician may observe the condition of the exposed part of the vagina wall and thus to see prolapses on the exposed wall. This would be unattainable for the conventional speculum without completely withdrawing the entire speculum, disassembling it, and using only one part as a spade for pressing on one wall of the vagina in order to expose the opposite wall for observation. If necessary, both removable blades 40 and 48 can be withdrawn in alternating sequence, or can be retracted both together to see if the uterus or the vaginal vault (dome) will drop further down. The degree of the drop of the uterus or the vaginal vault (dome)(if the uterus is gone) in relation to the hymeneal line can be measured with the calibrated retractable blade. This is easily done by positioning the tip of the sliding blade to the lowest edge of the prolapsing organ, i.e. cervix or vaginal vault or cystocele or rectocele and measuring from that distance to the level of the hymeneal line.

Some procedures may required that the physician must use only one blade. To accomplish this task, the physician may completely disconnect the entire upper part 22, from the lower part 24 sliding portion 26 by disengaging the projections 30 and 32 from respective slots 64 and 66 of the hook-like projection on the upper end of the fork-like sliding part 26. The upper part 22 can be disconnected from the speculum without removing the latter from the vagina or when the speculum is removed from the vagina.

When it is necessary to observe the vagina wall covered with the blade, then, without removing the speculum 20 from and without rotating it inside the vaginal cavity, the physician will slide the pin 72 along the longitudinal slot 68 to a position of a require circumferential slot, e.g., the slot 70a (FIG. 8) and is then turned in the circumferential slot 70a to a lateral position (FIGS. 8 and 9) for exposing the area of interest.

All manipulations described above, i.e., partial or complete withdrawal of the removable blades 40, 48, dilation of the vaginal cavity, complete disconnection of one of the guide parts of the speculum, etc., can be fulfilled without removing the speculum from the vaginal cavity.

If the speculum is intended for multiple use, complete disconnection of its parts facilitates its cleaning and storage.

Thus it has been shown that the vaginal speculum of the present invention allows complete disconnection of one of the blade guide parts or removal of the removable blade from the speculum without interrupting the procedure. The proposed vaginal speculum is convenient for cleaning, storage and packing and allows observation of the vaginal walls over the entire perimeter of the vaginal cavity without withdrawing, replacing or rotating the entire speculum. The vaginal speculum has blades moveable in axial as well as in circumferential direction.

Although the vaginal speculum of invention has been described in detail with reference to specific embodiments and drawings, it is understood that these embodiments do not limit the field of application of the invention and that any changes and modifications are possible, provided they do not go beyond the scope of the patent claims. For example, the hook and pin connection can be different from the one shown in the drawings and may be fulfilled, e.g., as a pin and sleeve connection with a sliding fit. The number of circumferential groove can vary from 1 to several. Both guide portions or only one of them may have replaceable removable blades.

What is claimed is:

1. A disconnectable vaginal speculum for observing the vagina of a female patient and for performing procedures in connection with treatments and measurements, comprising:

a first blade member having a longitudinal direction, a distal end and a proximal end with a first guide formed on said proximal end in a direction perpendicular to said longitudinal direction;

a sliding member slidingly guided in said first guide, said sliding member having first pivot connection means on one end and sliding member fixation means on the end opposite to said one end;

a second blade member having second pivot connection means for pivotally connecting and disconnecting said second blade member to and from said sliding means without removing said disconnectable vaginal speculum from said vagina;

said first blade member and said second blade member each consisting of a guide portion, which is not inserted into vagina of said female patient during the use of said disconnectable vaginal speculum, and a removable blade insertable into vagina of said female patient, said guide portion having a second guide parallel to said longitudinal direction, said removable blade being slidingly and removably inserted into said second guide; and means for fixing position of said second blade member with respect to said first blade member in any position to which said second blade member can be turned with the use of said pivot connection.

2. The speculum of claim 1, wherein said speculum is made of a transparent material.

3. The speculum of claim 2, further comprising measurement means for performing said measurements, said measurement means comprising a measurement scale formed on said removable blade.

4. The speculum of claim 1, further comprising blade turning means formed in said guide portion of said second blade member for turning said removable blade of said second blade member around an axis extending in said longitudinal direction.

5. The speculum of claim 3, further comprising blade turning means formed in said guide portion for turning said removable blade around an axis extending in said longitudinal direction.

6. The speculum of claim 1, wherein said first pivot connection means is made as a pair of L-shaped grooves and said second pivot means is made as a pair of pins slidingly insertable into said pair of L-shaped grooves, respectively.

7. The speculum of claim 3, wherein said first pivot connection means is made as a pair of L-shaped grooves and said second pivot means is made as a pair of pins slidingly insertable into said pair of L-shaped grooves, respectively.

8. The speculum of claim 4, wherein said blade turning means comprises a longitudinal slot formed in said guide portion parallel to said longitudinal direction and at least one circumferential slot which is perpendicular to said longitudinal slot formed in said guide portion of said second blade member and intersects therewith, said removable blade of said second blade member having a guide element which is rigidly connected to said removable blade of said second blade member and which can be guided in said longitudinal slot and in said circumferential slot.

9. The speculum of claim 5, wherein said blade turning means comprises a longitudinal slot formed in said guide portion parallel to said longitudinal direction and at least one circumferential slot which is perpendicular to said longitudinal slot formed in said guide portion of said second blade member and intersects therewith, said removable blade of said second blade member having a guide element which is rigidly connected to said removable blade of said second blade member and which can be guided in said longitudinal slot and in said circumferential slot.

10. The speculum of claim 6, wherein said blade turning means comprises a longitudinal slot formed in said guide portion parallel to said longitudinal direction and at least one circumferential slot which is perpendicular to said longitudinal slot formed in said guide portion of said second blade member and intersects therewith, said removable blade of said second blade member having a guide element which is rigidly connected to said removable blade of said second blade member and which can be guided in said longitudinal slot and in said circumferential slot.

11. The speculum of claim 7, wherein said blade turning means comprises a longitudinal slot formed in said guide portion parallel to said longitudinal direction and at least one circumferential slot which is perpendicular to said longitudinal slot formed in said guide portion of said second blade member and intersects therewith, said removable blade of said second blade member having a guide element which is rigidly connected to said removable blade of said second blade member and which can be guided in said longitudinal slot and in said circumferential slot.

12. The speculum of claim 1, wherein means for fixing position of said second blade member with respect to said first blade member comprises a projection with ratchet teeth formed on said sliding part and a projection with a pawl on said guide portion for engagement with said ratchet teeth.

13. The speculum of claim 8, wherein means for fixing position of said second blade member with respect to said first blade member comprises a projection with ratchet teeth formed on said sliding part and a projection with a pawl on said guide portion for engagement with said ratchet teeth.

14. The speculum of claim 9, wherein means for fixing position of said second blade member with respect to said first blade member comprises a projection with ratchet teeth formed on said sliding part and a projection with a pawl on said guide portion for engagement with said ratchet teeth.

15. The speculum of claim 10, wherein means for fixing position of said second blade member with respect to said first blade member comprises a projection with ratchet teeth formed on said sliding part and a projection with a pawl on said guide portion for engagement with said ratchet teeth.

16. The speculum of claim 11, wherein means for fixing position of said second blade member with respect to said first blade member comprises a projection with ratchet teeth formed on said sliding part and a projection with a pawl on said guide portion for engagement with said ratchet teeth.

17. The speculum of claim 1, wherein said first blade member has a distal end with a first semi-lens and said second blade member has a distal end with a second semi-lens, said first blade member and said second blade member can be turned with the use of said pivotal connection into a closed state in which said first semi-lens and said second semi-lens form a complete lens.

18. The speculum of claim 4, wherein said first blade member has a distal end with a first semi-lens and said second blade member has a distal end with a second semi-lens, said first blade member and said second blade member can be turned with the use of said pivotal connection into a closed state in which said first semi-lens and said second semi-lens form a complete lens.

19. The speculum of claim 6, wherein said first blade member has a distal end with a first semi-lens and said second blade member has a distal end with a second semi-lens, said first blade member and said second blade member can be turned with the use of said pivotal connection into a closed state in which said first semi-lens and said second semi-lens form a complete lens.

* * * * *